United States Patent [19]
Krespan

[11] Patent Number: 5,723,701
[45] Date of Patent: Mar. 3, 1998

[54] SATURATED LINEAR POLYFLUOROHYDROCARBONS, PROCESSES FOR THEIR PRODUCTION, AND THEIR USE IN CLEANING COMPOSITIONS

[75] Inventor: Carl George Krespan, Wilmington, Del.

[73] Assignee: E. I. du Pont de Nemours and Company, Wilmington, Del.

[21] Appl. No.: 460,021

[22] Filed: Jun. 2, 1995

Related U.S. Application Data

[62] Division of Ser. No. 919,454, Jul. 27, 1992, Pat. No. 5,504,265, which is a division of Ser. No. 595,840, Oct. 11, 1990, Pat. No. 5,171,902.

[51] Int. Cl.$^6$ ................................................ C07C 19/08
[52] U.S. Cl. ............................................................. 570/175
[58] Field of Search .................................................. 570/175

[56] References Cited

U.S. PATENT DOCUMENTS

| | | | |
|---|---|---|---|
| 2,550,953 | 5/1951 | Barrick | 260/648 |
| 2,704,715 | 3/1955 | Carroll et al. | 95/7 |
| 2,844,634 | 7/1958 | Neville et al. | 260/653 |
| 2,975,220 | 3/1961 | Hauptschein et al. | 260/653.1 |
| 2,999,815 | 9/1961 | Eisenman | 252/171 |
| 2,999,817 | 9/1961 | Bower | 252/172 |
| 3,042,727 | 7/1962 | Olstowski et al. | 260/653 |
| 3,573,213 | 3/1971 | Burt | 252/172 |
| 3,728,268 | 4/1973 | Burt | 252/170 |
| 3,789,006 | 1/1974 | McMillan et al. | 252/171 |
| 3,881,949 | 5/1975 | Brock | 134/31 |
| 3,903,009 | 9/1975 | Bauer et al. | 252/171 |
| 4,418,185 | 11/1983 | Throckmorton et al. | 526/201 |
| 4,559,154 | 12/1985 | Powell | 252/69 |
| 4,715,900 | 12/1987 | Connon et al. | 134/31 |
| 4,754,085 | 6/1988 | Gervasutti et al. | 570/175 |
| 4,828,751 | 5/1989 | Kremer | 252/171 |
| 4,902,839 | 2/1990 | Bielefeld et al. | 570/175 |
| 5,064,559 | 11/1991 | Merchant et al. | 252/171 |
| 5,064,560 | 11/1991 | Merchant | 252/171 |
| 5,097,082 | 3/1992 | Anton | 870/175 |
| 5,100,572 | 3/1992 | Merchant | 252/171 |
| 5,143,652 | 9/1992 | Slinn | 252/602 |
| 5,162,594 | 11/1992 | Krespan | 570/126 |
| 5,250,213 | 10/1993 | Rozen et al. | 252/162 |
| 5,346,645 | 9/1994 | Omure et al. | 252/194 |
| 5,531,916 | 7/1996 | Merchant | 510/412 |

FOREIGN PATENT DOCUMENTS

| | | | |
|---|---|---|---|
| 0 219 823 | 4/1987 | European Pat. Off. | |
| 0 324 478 | 7/1989 | European Pat. Off. | 570/176 |
| 1 578 933 | 11/1980 | United Kingdom. | |

OTHER PUBLICATIONS

Grinberg, V.A. et al, *Bull. of Acad. of Sci. of the USSR, Div. of Chem. Sci.*, 998–992 (1979).

Snegirev, V.F. et al, *Izvestiya Akad. Nauk SSSR, Seriya Khimicheskaya*, No. 12, pp. 2775–2781 (1983).

Li, J. et al, *Youji Huaxe*, 40–2, 24 (1984).

Knunyants, I.L. et al, *Izvestiya Akad. Nauk SSSR, Otdelenie Khimicheskikh Nauk*, No. 8, pp. 1412–1418 (1960).

Knunyants, I.L. et al, *Kinetika i Kataliz.*, 8(4), 834–840 (1967).

Pedler, A.E. et al, *J. Fluorine Chem.*, 1, 337–345 (1971/1972).

Hudlicky, M. et al, *J. Fluorine Chem.*, 44, pp. 345–359 (1989).

R.J. Chem. 19H170 (1991).

Hu, C.-M. et al, *J. Fluorine Chem.*, 46, 491–506 (1990).

*Primary Examiner*—Alan Siegel

[57] ABSTRACT

The compounds $CF_3CHFCHFCF_2CF_3$, $CF_3CH_2CHFCF_2CF_3$, $CF_3CHFCH_2CF_2CF_3$, $CF_3CHFCHFCF_2CF_2CF_3$, $CF_3CH_2CHFCF_2CF_2CF_3$, $CF_3CHFCH_2CF_2CF_2CF_3$, $CF_3CF_2CH_2CHFCF_2CF_3$, $CF_3CF_2CHFCHFCF_2CF_3$, $CF_3CHFCHFCF_2CF_2CF_3$, $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_2CF_3$; and compositions thereof. Catalytic processes using Group VIII metals are disclosed for reacting selected olefinic starting materials with hydrogen to produce as the major products dihydropolyfluoroalkanes or trihydropolyfluoroalkanes wherein the hydrogens are positioned on two adjacent carbon atoms; as are processes using iodine and/or hydrogen iodide in the reduction of selected olefinic starting materials to dihydropolyfluoroalkanes or trihydropolyfluoroalkanes.

20 Claims, No Drawings

SATURATED LINEAR POLYFLUOROHYDROCARBONS, PROCESSES FOR THEIR PRODUCTION, AND THEIR USE IN CLEANING COMPOSITIONS

This is a division of application Ser. No. 07/919,454, filed Jul. 27, 1992 now U.S. Pat. No. 5,504,285 which is a division of application Ser. No. 07/595,840, filed Oct. 11, 1990 and issued as U.S. Pat. No. 5,171,902.

FIELD OF THE INVENTION

This invention relates to fluorine-substituted hydrocarbon compounds, their production, and their use for cleaning solid surfaces, and more particularly to polyfluoropentanes, polyfluorohexanes, and polyfluoroheptanes, their production by the reduction of polyfluoroolefin starting materials, and their use as solvents.

BACKGROUND OF THE INVENTION

Various organic solvents have been used as cleaning liquids for the removal of contaminants from contaminated articles and materials. Certain fluorine-containing organic compounds such as 1,1,2-trichloro-1,2,2-trifluoroethane have been reported as useful for this purpose, particularly with regard to cleaning organic polymers and plastics which may be sensitive to other more common and more powerful solvents such as trichloroethylene or perchloroethylene. Recently, however, there have been efforts to reduce the use of certain compounds such as trichlorotrifluoroethane which also contain chlorine because of a concern over their potential to deplete ozone, and to thereby affect the layer of ozone that is considered important in protecting the earth's surface from ultraviolet radiation.

Boiling point, flammability and solvent power can often be adjusted by preparing mixtures of solvents. For example, certain mixtures of 1,1,2-trichloro-1,2,2-trifluoroethane with other solvents (e.g., isopropanol and nitromethane) have been reported as useful in removing contaminants which are not removed by 1,1,2-trichloro-1,2,2-trifluoroethane alone, and in cleaning articles such as electronic circuit boards where the requirements for a cleaning solvent are relatively stringent, (i.e., it is generally desirable in circuit board cleaning to use solvents which have low boiling points, are non-flammable, have low toxicity, and have high solvent power so that flux such as rosin and flux residues which result from soldering electronic components to the circuit board can be removed without damage to the circuit board substrate).

While boiling, flammability, and solvent power can often be adjusted by preparing mixtures of solvents, the utility of the resulting mixtures can be limited for certain applications because the mixtures fractionate to an undesirable degree during use. Mixtures can also fractionate during recovery, making it more difficult to recover a solvent mixture with the original composition. Azeotropic compositions, with their constant boiling and constant composition characteristics, are thus considered particularly useful.

Azeotropic compositions exhibit either a maximum or minimum boiling point and do not fractionate upon boiling. These characteristics are also important in the use of the solvent compositions in certain cleaning operations, such as removing solder fluxes and flux residues from printed circuit boards. Preferential evaporation of the more volatile components of the solvent mixtures, which would be the case if the mixtures were not azeotropes, or azeotrope-like, would result in mixtures with changed compositions which may have less desirable properties (e.g., lower solvency for contaminants such as rosin fluxes and/or less inertness toward the substrates such as electrical components).

Azeotropic characteristics are also desirable in vapor degreasing operations where redistilled material is usually used for final rinse-cleaning. Thus, the vapor defluxing or degreasing system acts as a still. Unless the solvent composition exhibits a constant boiling point (i.e., is an azeotrope or is azeotrope-like) fractionation will occur and undesirable solvent distribution may act to upset the safety and effectiveness of the cleaning operation.

A number of azeotropic compositions based upon halohydrocarbons containing fluorine have been discovered and in some cases used as solvents for the removal of solder fluxes and flux residues from printed circuit boards and for miscellaneous vapor degreasing applications. For example, U.S. Pat. No. 2,999,815 discloses the azeotrope of 1,1,2-trichloro-1,2,2-trifluoroethane with acetone; U.S. Pat. No. 3,903,009 discloses a ternary azeotrope of 1,1,2-trichloro-1,2,2-trifluoroethane with nitromethane and ethanol; U.S. Pat. No. 3,573,213 discloses an azeotrope of 1,1,2-trichloro-1,2,2-trifluoroethane with nitromethane; U.S. Pat. No. 3,789,006 discloses the ternary azeotrope of 1,1,2-trichloro-1,2,2-trifluoroethane with nitromethane and isopropanol; U.S. Pat. No. 3,728,268 discloses the ternary azeotrope of 1,1,2-trichloro-1,2,2-trifluoroethane with acetone and ethanol; U.S. Pat. No. 2,999,817 discloses the binary azeotrope of 1,1,2-trichloro-1,2,2-trifluoroethane and methylene chloride (i.e., dichloromethane); and U.S. Pat. No. 4,715,900 discloses ternary compositions of trichlorotrifluoroethane, dichlorodifluoroethane, and ethanol or methanol.

As noted above, many solvent compositions which have proven useful for cleaning contain at least one component which is a halogen-substituted hydrocarbon containing chlorine, and there have been concerns raised over the ozone depletion potential of halogen-substituted hydrocarbons which contain chlorine. Efforts are being made to develop compositions which may at least partially replace the chlorine containing components with other components having lower potential for ozone depletion. Azeotropic compositions of this type are of particular interest.

Means of synthesizing various fluorine-substituted alkanes have been reported.

U.S. Pat. No. 2,550,953 discloses catalytic hydrogenation of unsaturated fluorohydrocarbons.

U.S. Pat. No. 2,844,636 discloses that 1,1,2,3,4,4-hexafluorobutene can be made by reacting perfluorocyclobutene with hydrogen, using elemental iodine as the catalyst.

V. A. Grinberg et al., Bulletin of the Academy of Sciences of the USSR, Division of Chemical Science, 988 (1979) report the synthesis of 3,4-dihydro perfluorohexane, $CF_3CF_2CHFCHFCF_2CF_3$, by the electrochemical reaction of trifluoroacetic acid, sodium trifluoroacetate and trifluoroethylene in aqueous acetonitrile as 5% of a three-component mixture that was isolated in 30% of the theoretical (based on current) amount.

V. F. Snegirev et al., Izvestiya Akademii Nauk SSSR, Seriya Khimicheskaya, 1983, No. 12, pp. 2775–2781, report the reduction of the branched perfluoroolefins, perfluoro-4-methyl-2-pentene and perfluoro-2-methyl-2-pentene to mono-, di- and trihydro derivatives by metal hydride complexes or by hydrogenation over a palladium/carbon catalyst.

J. Li et al., Youji Huaxue, 1984, 40–2, p. 24, report the palladium on alumina catalyzed hydrogenation of hexafluoropropylene dimers to give dihydro and trihydro reduction products.

I. L. Knunyants et al., Izvestiya Akademii Nauk SSSR, Otdelenie Khimicheskikh Nauk, 1960, No 8, pp. 1412–1418 discusses the catalytic hydrogenation of perfluoroethylene, propene and butenes.

U.S. Pat. No. 4,902,839 discloses certain tetrahydro derivatives of perfluorobutanes, perfluoropentanes and perfluorohexanes, as well as processes for their preparation.

SUMMARY OF THE INVENTION

In accordance with this invention, novel compounds are provided which contain no chlorine and which may be used alone or in combination with other miscible solvents (e.g., alcohols, ethers, esters, ketones, nitrogen-containing organic compounds such as acetonitrile and nitromethane, and halogenated hydrocarbons) as agents for cleaning solid surfaces.

The novel compounds of this invention include the group of linear dihydro and trihydro polyfluoropentanes, polyfluorohexanes and polyfluoroheptanes represented by the structural formulae $CF_3CHFCHFCF_2CF_3$, $CF_3CH_2CHFCF_2CF_3$, $CF_3CHFCH_2CF_2CF_3$, $CF_3CHFCHFCF_2CF_2CF_3$, $CF_3CH_2CHFCF_2CF_2$, $CF_3CHFCH_2CF_2CF_3$, $CF_3CF_2CH_2CHFCF_2CF_3$, $CF_3CF_2CHFCHFCF_2CF_3$, $CF_3CHFCHFCF_2CF_2CF_2CF_3$, $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_3$.

A process is provided in accordance with this invention for preparing a linear trihydropolyfluoroalkane selected from the group consisting of $CF_3CH_2CHFCF_2CF_3$, $CF_3CHFCH_2CF_2CF_3$, $CF_3CH_2CHFCF_2CF_2CF_3$, $CF_3CHFCH_2CF_2CF_2CF_3$, $CF_3CF_2CH_2CHFCF_2CF_3$, $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_2CF_3$, which comprises the step of reacting an olefinic starting material in the liquid phase with hydrogen over a Group VIII metal catalyst (preferably in the presence of a polar solvent); wherein said olefinic starting material has the same number of carbon atoms as said trihydropolyfluoroalkane and is selected from the group of perfluoroolefins consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_3$; and wherein said olefinic starting material has its olefinic bond between the carbon atoms which correspond to the carbons which bear the hydrogen in said trihydroxzpolyfluoroalkane.

Another process is provided in accordance with this invention for preparing a linear trihydropolyfluoroalkane selected from the group consisting of $CF_3CH_2CHFCF_2CF_3$, $CF_3CHFCH_2CF_2CF_3$, $CF_3CH_2CHFCF_2CF_2CF_3$, $CF_3CHFCH_2CF_2CF_2CF_3$, $CF_3CF_2CH_2CHFCF_2CF_3$, $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_2CF_3$, which comprises the step of reacting an olefinic starting material at an elevated temperature with hydrogen in the presence of at least one material selected from the group consisting of iodine and hydrogen iodide or with hydrogen iodide; wherein said olefinic starting material has the same number of carbon atoms as said trihydropolyfluoroalkane and is selected from the group consisting of $CF_3CH=CFCF_2CF_3$, $CF_3CF=CHCF_2CF_3$, $CF_3CH=CFCF_2CF_2CF_3$, $CF_3CF=CHCF_2CF_2CF_3$, $CF_3CF_2CH=CFCF_2CF_3$, $CF_3CF_2CH=CFCF_2CF_2CF_3$, $CF_3CF_2CF=CHCF_2CF_2CF_3$, $CF_3CH=CFCF_2CF_2CF_3$, and $CF_3CF=CHCF_2CF_2CF_2CF_3$; and wherein said olefinic starting material has its olefinic bond between the carbon atoms which correspond to the carbons which bear the hydrogen in said trihydropolyfluoroalkane.

In accordance with this invention a process is also provided for preparing a linear dihydropolyfluoroalkane selected from the group consisting of $CF_3CHFCHFCF_2CF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material in the vapor phase with hydrogen over a Group VIII metal catalyst; wherein said olefinic starting material has the same number of carbon atoms as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_3$; and wherein said olefinic starting material has its olefinic bond between the carbon atoms which correspond to the carbons which bear the hydrogen in said dihydropolyfluoroalkane.

Another process is provided in accordance with this invention for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material in the liquid phase with hydrogen over a Group VIII metal catalyst (preferably in the absence of a polar solvent); wherein said olefinic starting material has the same number of carbon atoms as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_3$; and wherein said olefinic starting material has its olefinic bond between the carbon atoms which correspond to the carbons which bear the hydrogen in said dihydropolyfluoroalkane.

A third process is provided in accordance with this invention for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material at an elevated temperature with hydrogen in the presence of at least one material selected from the group consisting of iodine and hydrogen iodide or with hydrogen iodide; wherein said olefinic starting material has the same number of carbon atoms as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_3$; and wherein said olefinic starting material has its olefinic bond between the carbon atoms which correspond to the carbons which bear the hydrogen in said dihydropolyfluoroalkane.

DETAILED DESCRIPTION OF THE INVENTION

This invention provides novel saturated linear polyfluorohydrocarbons (i.e., polyfluoroalkanes) which contain two or three hydrogen atoms per molecule. The trihydropolyfluoroalkanes of this invention include the trihydropolyfluoropentanes represented by the structural formulae $CF_3CH_2CHFCF_2CF_3$ and $CF_3CHFCH_2CF_2CF_3$; the trihydropolyfluorohexanes represented by the structural formulae $CF_3CH_2CHFCF_2CF_2CF_3$, $CF_3CHFCH_2CF_2CF_2CF_3$, and $CF_3CF_2CH_2CHFCF_2CF_3$; and the trihydropolyfluoroheptanes represented by the structural formulae $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_2CF_3$.

A process is provided in accordance with this invention for preparing these trihydropolyfluoroalkanes which comprises the step of reacting an olefinic starting material in the liquid phase with hydrogen over a Group VIII metal catalyst, preferably from the palladium group (i.e., Pd, Rh and/or Ru). Palladium and rhodium are the more preferred metals, with palladium being most preferred. The metal catalyst may be supported, for example on carbon or on alumina. The olefinic starting material used for this process has the same number of carbon atoms as the desired trihydropolyfluoroalkane and is selected from the group of perfluoroolefins consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$. Thus, a polyfluoroalkane selected from the group consisting of $CF_3CH_2CHFCF_2CF_3$ and $CF_3CHFCH_2CF_2CF_3$ can be produced by hydrogenating $CF_3CF=CFCF_2CF_3$ over a metal catalyst in accordance with this invention; a polyfluoroalkane selected from the group consisting of $CF_3CH_2CHFCF_2CF_2CF_3$, $CF_3CHFCH_2CF_2CF_2CF_3$, and $CF_3CF_2CH_2CHFCF_2CF_3$ can be produced by hydrogenating a starting material selected from the group consisting of $CF_3CF=CFCF_2CF_2CF_3$ and $CF_3CF_2CF=CFCF_2CF_3$ over a metal catalyst in accordance with this invention; and a polyfluoroalkane selected from the group consisting of $CF_3CHFCH_2CF_2CF_2CF_2CF_3$, $CF_3CH_2CHFCF_2CF_2CF_2CF_3$ and $CF_3CF_2CH_2CHFCF_2CF_2CF_3$ can be produced by hydrogenating a starting material selected from the group consisting of $CF_3CF_2CF=CFCF_2CF_2CF_3$ and $CF_3CF=CFCF_2CF_2CF_2CF_3$ over a metal catalyst in accordance with this invention. In any case the olefinic starting material should have its olefinic bond between the carbon atoms which correspond to the carbons which bear the hydrogen in the desired trihydropolyfluoroalkane.

The reduction can be carried out at temperatures in the range of from about 0° C. to about 200° C. The preferred temperature range is from about 25° C. to about 100° C. The pressure of the hydrogenation may be within a wide range, from less than 1 atmosphere to extremely high pressures, but normally pressures from 1 atmosphere to about 10 atmospheres is preferred. The molar ratio of hydrogen to olefinic starting material for this process is preferably between about 1:1 and 100:1; and is more preferably between about 2:1 and 10:1. For batch processes, the hydrogen may be provided by continuous or intermittent addition to a reactor containing the olefinic starting material and the catalyst until the desired ratio (based upon the initial amount of starting material) is attained.

The hydrogenation is preferably conducted in the presence of a polar solvent. The presence of a polar solvent is essential for high selectivity to the trihydro derivatives from the perfluoroolefin starting materials. Suitable polar solvents which may be employed include water, alcohols, glycol, acetic acid, dimethylformamide, N-methyl pyrollidone and triethylamine, or mixtures thereof. Methanol is a preferred polar solvent.

The olefinic starting materials for this process may be prepared in accordance with the teachings of U.S. patent application Ser. No. 07/595,839 (see U.S. Pat. No. 5,162,594 which issued pursuant to a continuation-in-part thereof) which is hereby incorporated by reference in its entirety. According to the teachings therein, polyfluoroolefins having at least 5 carbon atoms may be manufactured by reacting together two selected polyfluoroolefins in the presence of a catalyst of the formula $AlX_3$ where X is one or more of F, Cl or Br (provided that X is not entirely F). As exemplified by Example A herein, a five carbon perfluoroolefinic starting material may be prepared by the reaction of hexafluoropropene (HFP) with tetrafluoroethylene (TFE). Six carbon perfluoro-olefinic starting materials may be prepared by the reaction, substantially according to the procedure of Example A, of 1,1,1,4,4,4-hexafluoro-2,3-dichloro-2-butene with TFE to yield an intermediate product comprising perfluoro-2,3-dichloro-2-hexene which may then be converted to a mixture of perfluoro-2-hexene and perfluoro-3-hexene by reaction with potassium fluoride in refluxing N-methyl pyrolidone. A mixture of seven carbon perfluoroolefinic starting materials may be prepared by the reaction, substantially according to the procedure of Example A, of hexafluoro-propene with 2 moles of TFE.

Another process is provided in accordance with this invention for preparing a linear trihydropolyfluoroalkane selected from the group consisting of $CF_3CH_2CHFCF_2CF_3$, $CF_3CHFCH_2CF_2CF_3$, $CF_3CH_2CHFCF_2CF_2CF_3$, $CF_3CHFCH_2CF_2CF_2CF_3$, $CF_3CF_2CH_2CHFCF_2CF_3$, $CF_3CHFCH_2CF_2CF_2CF_2CF_3$, $CF_3CH_2CHFCF_2CF_2CF_2CF_3$, $CF_3CF_2CHFCH_2CF_2CF_2CF_3$, and $CF_3CF_2CH_2CHFCF_2CF_2CF_3$, which comprises the step of reacting an olefinic starting material at an elevated temperature with hydrogen in the presence of at least one material selected from the group consisting of iodine and hydrogen iodide or with hydrogen iodide; wherein said olefinic starting material has the same number of carbon atoms as said trihydropolyfluoroalkane and is selected from the group consisting of $CF_3CH=CFCF_2CF_3$, $CF_3CF=CHCF_2CF_3$, $CF_3CH=CFCF_2CF_2CF_3$, $CF_3CF=CHCF_2CF_2CF_3$, $CF_3CF_2CH=CFCF_2CF_3$, $CF_3CF_2CH=CFCF_2CF_2CF_3$, $CF_3CF_2CF=CHCF_2CF_2CF_3$, $CF_3CH=CFCF=2CF_2CF_2CF_3$, and $CF_3CF=CHCF_2CF_2CF_2CF_3$; and wherein said olefinic starting material has its olefinic bond between the carbon atoms which correspond to the carbons which bear the hydrogen in said trihydropolyfluoroalkane. The hydrogen-containing olefinic starting materials may be made substantially according to the procedure of Example A, but using monohydro compounds rather than perfluoro compounds (e.g., 2H-pentafluoropropene rather than HFP).

Iodine and/or HI is used for this hydrogenation in accordance with the teachings of U.S. patent application Ser. No. 07/533,333. (see U.S. Pat. No. 5,092,082 which issued pursuant to a continuation-in-part thereof). Hydrogen iodide for the reaction may be provided by several methods. For example, the reaction may be run with stoichiometric HI. Alternatively, the reaction may be run with catalytic amounts of HI in the presence of hydrogen. The reaction may also be run with hydrogen using catalytic amounts of iodine. This latter method is preferred for batch reactions and for ease of handling. This reaction may be accomplished in the absence of supported metal catalysts; and indeed the catalyst for this reaction typically consists essentially of iodine and/or hydrogen iodide. The reaction temperature for this reaction should generally be from 100° C. to 500° C. A preferred temperature range is from 200° C. to 400° C. This reaction may be run at a pressure of from about 50 psi to 5000 psi, with 500 psi to 1500 psi being preferred.

The amount of hydrogen provided for contact with the olefinic starting material (either by addition of HI or by feed of $H_2$ gas) should represent at least one molecule of hydrogen for each olefinic bond to be saturated, and is preferably 10 times said minimum, or less (i.e., the molar ratio of hydrogen available for reacting to olefinic starting material is preferably between 10:1 and 1:1). When hydrogen gas is used, the hydrogen can be fed either in the pure state or diluted with an inert gas (e.g., nitrogen, helium or argon).

The dihydropolyfluoroalkanes of this invention include the dihydropolyfluoropentane represented by the structural formula $CF_3CHFCHFCF_2CF_3$; the dihydropolyfluorohexane represented by the structural formula $CF_3CHFCHFCF_2CF_2CF_3$; and the dihydropolyfluoroheptanes represented by the structural formulae $CF_3CF_2CHFCHFCF_2CF_2CF_3$ and $CF_3CHFCHFCF_2CF_2CF_2CF_3$.

A process is provided in accordance with this invention for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material in the vapor phase with hydrogen over a Group VIII metal catalyst. Preferably the catalyst is from the palladium group. The olefinic starting material for this process has the same number of carbon atoms as the desired dihydropolyfluoroalkanes and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$; and has its olefinic bond between the carbon atoms which correspond to the carbons which bear the hydrogen in said dihydropolyfluoroalkane.

Unsupported metal catalysts and supported metal catalysts wherein the metal is palladium, rhodium, or ruthenium are particularly suitable for use in this process. Supports such as carbon or alumina may be employed. Supported palladium catalysts are preferred.

The vapor phase reduction can be carried out at temperatures in the range of from about 50° C. to about 250° C.; the preferred temperature range is from about 100° C. to about 200° C. The pressure of the hydrogenation may vary widely from less than 1 atmosphere to 20 or more atmospheres. The molar ratio of hydrogen to olefinic starting material for this process is preferably between about 0.5:1 and 4:1, and is more preferably between about 0.5:1 and 1.5:1.

Another process is provided in accordance with this invention for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material in the liquid phase with hydrogen over a Group VIII metal catalyst (preferably from the palladium group); wherein said olefinic starting material has the same number of carbon atoms as said dihydropolyfluoroakane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$; and wherein said olefinic starting material has its olefinic bond between the carbon atoms which correspond to the carbons which bear the hydrogen in said dihydropolyfluoroalkane.

Palladium and rhodium are the preferred metals, with palladium being the most preferred. The metal catalysts may be supported, for example, on carbon or on alumina, with carbon the preferred support.

The liquid phase reduction can be carried out at temperatures ranging from about 0° C. to 200° C., with a preferred range being from about 25° C. to about 100° C. The pressure of the hydrogenation may vary widely from less than 1 atmosphere to 30 atmospheres or more. The molar ratio of hydrogen to olefinic starting material for this process is preferably between about 1:1 and 100:1 and is more preferably between about 1:1 and 10:1.

This hydrogenation is preferably carried out in the absence of a polar solvent. The reduction may be carried out neat (i.e., using no solvent or diluent) or in the presence of a non-polar solvent. Suitable non-polar solvents which may be employed include inert low dielectric alkanes (e.g., nonane and cyclohexane) or low dielectric aromatics (e.g., toluene, benzene and orthoxylene).

Another process is provided in accordance with this invention for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, which comprises the step of reacting an olefinic starting material which has the same number of carbons as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$, at an elevated temperature with hydrogen in the presence of at least one material selected from the group consisting of iodine and hydrogen iodide or with hydrogen iodide. The olefinic starting material should have its olefinic bond between the carbon atoms which correspond to the carbons which bear the hydrogen in the desired dihydropolyfluoroalkane.

Iodine and/or HI is used for this hydrogenation in accordance with the teachings of U.S. patent application Ser. No. 07/533,333. Hydrogen iodide for the reaction may be provided by several methods. For example, the reaction may be run with stoichiometric HI. Alternatively, the reaction may be run with catalytic amounts of HI in the presence of hydrogen. The reaction may also be run with hydrogen using catalytic amounts of iodine. This latter method is preferred for batch reactions and for ease of handling. This reaction may be accomplished in the absence of supported metal catalysts; and indeed the catalyst for this reaction typically consists essentially of iodine and/or hydrogen iodide. The reaction temperature for this reaction should generally be from 100° C. to 500° C. A preferred temperature range is from 200° C. to 400° C. This reaction may be run at a pressure of from about 50 psi to 5000 psi, with 500 psi to 1500 psi being preferred.

The amount of hydrogen provided for contact with the olefinic starting material (either by addition of HI or by feed of $H_2$ gas) should represent at least one molecule of hydrogen for each olefinic bond to be saturated, and is preferably 10 times said minimum, or less (i.e., the molar ratio of hydrogen available for reacting to olefinic starting material is preferably between 10:1 and 1:1). When hydrogen gas is used, the hydrogen can be fed either in the pure state or diluted with an inert gas (e.g., nitrogen, helium or argon).

The processes of this invention wherein the olefinic starting material is hydrogenated over a palladium group metal catalyst, allow for selecting between processes wherein the major product (i.e., above 50 mole percent based upon the amount of olefinic starting material hydrogenated) is a dihydropolyfluoroalkane, and processes wherein the major product is a trihydropolyfluoroalkane. In particular, liquid phase processes wherein polar solvents are used favor the production of trihydropolyfluoroalkanes and may thus be used to produce trihydropolyfluoroalkanes as the major product. In a preferred process, where high yield of trihydropolyfluoroalkanes is desired, a liquid phase process using polar solvents may be used to produce about 65 mole percent or more trihydropolyfluoroalkane product. Examples 1, 2, 4, 7, 10 and 15 herein are referenced as examples of trihydrononafluoropentane preparation On the other hand vapor phase processes, neat liquid phase processes, and liquid phase processes using non-polar solvents (i.e., processes essentially free of polar solvents) favor production of dihydropolyfluoroalkanes and may thus be used to produce dihydropolyfluoroalkanes as the major product of the reaction. In a preferred process, where high yield of dihydropolyfluoroalkanes is desired, a vapor phase process, a neat liquid process, or a liquid phase process using non-polar solvents may be used to produce about 65 mole percent or more dihydropolyfluoroalkane product. Examples 5, 6, 8, 9, 11, 12, 13 and 14 herein are referenced as examples of dihydropolyfluoroalkane preparation. Examples 13 and 14 indicate further that the use of an appropriate solvent can result in the formation of one diastereomeric dihydro compound selectively. Example 8 illustrates the high selectivity for introduction of two hydrogens which is possible in a vapor phase reaction using a palladium catalyst.

The processes of this invention which do not use metal catalysts and which react olefinic starting material with hydrogen in the presence of iodine and/or hydrogen iodide or with hydrogen iodide, allow for producing as the major product a polyfluoroalkane wherein exactly two hydrogens have been added to said olefinic starting material. In a preferred process, where high yield of polyfluoroalkane wherein exactly two hydrogens have been added to an olefinic starting material is desired, the processes using iodine and/or hydrogen iodide may be used to produce about 95 mole percent or more of product wherein exactly two hydrogens have been added to the olefinic starting material. For example, 2,3-dihydrodecafluoropentane of over 99% purity can be obtained by the reaction of one part perfluoropentene-2 with excess hydrogen and about 0.5 part of iodine at 300° C. and 1000 psi for 20 hours (see Example 3 herein).

The dihydro and trihydro linear polyfluoropentanes, polyfluorohexanes and polyfluoroheptanes of this invention are useful as solvents (especially those compounds having boiling points of 100° C. or less). They are replacements for currently environmentally suspect chlorofluorocarbons such as trichlorotrifluoroethane. They have zero ozone depletion potential. They are non-flammable. These polyfluoroalkanes may be used by themselves or in combination with other miscible solvents as cleaning agents or defluxing agents for solid surfaces, for example, printed wire boards. The compounds having boiling points above 75° C. are useful as vapor degreasers. The compounds of this invention may also be used as drying agents.

The dihydropolyfluoroalkanes and trihydropolyfluoroalkanes of this invention are miscible with various solvents conventionally used in cleaning operations. Compositions suitable for use in cleaning operations can be prepared which comprise a mixture of dihydro- and/or trihydropolyfluoroalkanes of this invention with one or more compounds selected from the group consisting of alcohols, ethers, esters, ketones, nitromethane, acetonitrile, and halogenated hydrocarbons. The preferred alcohols and halogenated hydrocarbons contain from 1 to 4 carbon atoms; the preferred ethers contain from 2 to 6 carbon atoms; and the preferred esters and ketones contain from 3 to 6 carbon atoms. Examples of suitable alcohols include methanol, ethanol and isopropanol. Examples of suitable ethers include tetrahydrofuran and diethylether. Examples of suitable ketones include acetone and methylethylketone. Examples of suitable halogenated hydrocarbons include methylene chloride (i.e., dichloromethane), 1,1,2-trichloro-1,2,2-trifluoroethane, dichlorodifluoroethane, trichloroethene, and trans-1,2-dichloroethylene. Preferably, such compositions contain at least about 5 percent by weight total of the polyfluoroalkanes of this invention; and can contain up to 99 percent by weight, or even more thereof. Preferred compositions include mixtures of $CF_3CHFCHFCF_2CF_3$, $CF_3CH_2CHFCF_2CF_3$ or $CF_3CHFCH_2CF_2CF_3$(especially $CF_3CHFCHFCF_2CF_3$) with one or more of said alcohols, ethers, esters, ketones, nitromethane, acetonitrile and halogenated hydrocarbons. Most preferred with respect to ozone depletion potential are compositions in which no component contains chlorine.

The mixtures of this invention are useful in a wide variety of processes for cleaning solid surfaces which comprise treating said surface therewith. Applications include removal of flux and flux residues from printed circuit boards contaminated therewith.

Compositions which comprise an admixture of effective amounts of one or more of the dihydropolyfluoroalkanes and trihydropolyfluoroalkanes of this invention with one or more solvents selected from the group consisting of alcohols, ethers, esters, ketones, nitromethane, acetonitrile and halogenated hydrocarbons to form an azeotrope or azeotrope-like mixture are considered especially useful. Reference is made to U.S. patent application Ser. No. 07/595,833 (see U.S. Pat. No. 5,064,559 which issued pursuant thereto and to U.S. patent application Ser. No. 07/595,834 (see U.S. Pat. No. 5,064,560 which issued pursuant thereto for providing examples of certain azeotrope admixtures. In particular, azeotropic compositions consisting essentially of about 95.3 weight percent $CF_3CHFCHFCF_2CF_3$ and about 4.7 weight percent methanol (boiling point about 39.9° C.); consisting essentially of about 97.1 weight percent $CF_3CHFCHFCF_2CF_3$ and about 2.9 weight percent ethanol (boiling point about 43.4° C.); consisting essentially of about 97.4 weight percent $CF_3CHFCHFCF_2CF_3$ and about 2.6 weight isopropanol (boiling point about 45.5° C.); consisting essentially of about 60.5 weight percent $CF_3CHFCHFCF_2CF_3$, about 36.2 weight percent trans 1,2-dichloroethylene, and about 3.3 weight percent methanol (boiling point about 35.3° C.); and consisting essentially of about 63.9 weight percent $CF_3CHFCHFCF_2CF_3$, about 35.1 weight percent trans 1,2-dichloroethylene and about 1.0 weight percent ethanol (boiling point about 35.1° C.) are considered useful for cleaning printed circuit board contaminated with flux and flux-residues.

The compositions of the invention may be used in conventional apparatus, employing conventional operating techniques. The solvent(s) may be used without heat if desired, but the cleaning action of the solvent may be assisted by conventional means (e.g., heating, agitation, etc.). In some applications (e.g., removing certain tenacious fluxes from soldered components) it may be advantageous to use ultrasonic irradiation in combination with the solvent(s).

Compositions provided in accordance with this invention can be used in cleaning processes such as is described in U.S. Pat. No. 3,881,949 and U.S. Pat. No. 4,715,900, both of which are incorporated herein by reference.

The mixtures of the instant invention can be prepared by any convenient method including mixing or combining the desired amounts of the components. A preferred method is to weigh the desired amounts of each component and thereafter combine them in an appropriate container.

Practice of the invention will become further apparent from the following non-limiting examples.

EXAMPLE A

Preparation of $CF_3CF=CFCF_2CF_3$ (F-Pentene-2)

A 400-mL metal tube charged at $-20°$ C. with 8.0 g of $AlF_{2.8}Cl_{0.2}$ (prepared from $AlCl_3+CFCl_3$), 75 g (0.50 mol) of hexafluoropropene, and 50 g (0.50 mol) of tetrafluoroethylene was shaken for 30 min. while the temperature rose quickly to $20°$ C. and the pressure dropped to 8 psi. Distillation of the product afforded 88.0 g (70%) of F-pentene-2, b.p. $23°-26°$ C., identified by IR, NMR and GC/MS. NMR showed the product to be 89% trans-isomer and 11% cis-isomer.

EXAMPLE 1

Reduction of Perfluoro-pentene-2 (F-pentene-2; $CF_3CF=CFCF_2CF_3$)

A 1-L metal tube charged with 86 g (0.34 mol) of F-pentene-2, 300 mL of absolute ethanol, and 5 g of 5% Pd on carbon was agitated at $25°$ C. under 50–100 psi of hydrogen until the pressure drop was 0 after 14 hr. The tube was cooled to $0°$ C., gases were bled, and the cold reaction mixture was pressure-filtered under $N_2$. Distillation gave product, bp mainly $43°-46°$ C., which co-distilled with a small amount of ethanol. The crude product contained trihydrononafluoropentane (2 isomers) and dihydrodecafluoropentane in a weight ratio of about 77:23. After a water wash to remove ethanol, the product (59 g) was dried over $MgSO_4$, filtered and fractionated. A foreshot, bp $27°-28°$ C., was shown by $^1H$ and $^{19}F$ NMR to be a mixture of cis- and trans-F-pentene-2, $Z—CF_3CH=CFCF_2CF_3$, and $Z-CF_3CF=CHCF_2CF_3$. This was followed by 37 g of cuts, bp $46°-53°$ C., increasingly rich in F-2H,3H-pentane and containing less F-2H,2H,3H-pentane and F-2H,3H,3H-pentane. Identification was by GC/MS and NMR.

The product mixture of this example was shown (by further exposing it to hydrogen in the presence of a Pd/C catalyst) to be stable to reduction conditions once it is formed, indicating that loss of $F^-$ or HF leading to trihydro product occurs while the olefin is reacting on the catalyst surface.

EXAMPLE 2

Reduction of $CF_3CF=CFCF_2CF_3$

A 500 mL heavy-walled bottle charged at $0°$ C. with 4 g of 5% Pd on carbon catalyst, 150 mL of absolute ethanol, and 145 g (0.58 mol) of perfluoropentene-2 was attached to a Parr hydrogenation apparatus and pressured to 50 psi with hydrogen. The reaction mixture was shaken at $25°$ C. and occasionally repressured with hydrogen until the rate of pressure drop had greatly slowed (8 hr). Distillation gave 130.1 g of a foreshot rich in product, bp $26°-77°$ C., which was combined with 58.1 g of foreshot from a similar reduction of 77 g (0.308 mol) of perfluoropentene-2, washed with 100 mL of water, dried over $CaCl_2$, filtered, and distilled. The product so obtained, bp $49°-51°$ C., 128.3 g, was shown by GC to consist of about 82 wt-% of trihydro derivatives $CF_3CH_2CHFCF_2CF_3/CF_3CHFCH_2CF_2CF_3$ and 18 wt-% of $CF_3CHFCHFCF_2CF_3$, the latter composed of two diastereomers in 96:4 ratio. Analysis by proton NMR indicated 84 mol-% of trihydro derivatives perfluoro-2H, 2H,3H-pentane and perfluoro-2H,3H,3H-pentane in 86:14 ratio, along with 16 mol-% of perfluoro-2H,3H-pentane diastereomers.

EXAMPLE 3

Reduction of $CF_3CF=CFCF_2CF_3$

A metal rocker tube charged with 97.4 g (0.384 mol) of iodine and 191.8 g (0.767 mol) of perfluoropentene-2 was cooled, evacuated, pressured with 100 psi of hydrogen, and heated to $300°$ C. Hydrogen pressure was raised to 1000 psi and maintained there while the vessel was kept at $300°$ C. for 1 day. The vessel was cooled to $5°$ C., gases were vented, and the cold product (157.2 g, 99% pure by GC) was washed with cold aqueous $Na_2S_2O_3$, dried over $Na_2SO_4$, to give perfluoro-2H,3H-pentane, bp $43°-52°$ C., as two diastereomers in 49:51 ratio.

EXAMPLE 4

Reduction of $CF_3CF=CFCF_2CF_3$

A Parr hydrogenator charged cold with 6.0 g of 0.5% Pd on alumina spheres, 20.4 g (0.082 mol) of perfluoropentene-2, and 100 mL of absolute ethanol was purged three times with $N_2$ and pressurized to 45 psi with hydrogen. The mixture was shaken for 12 hours at $25°$ C. while hydrogen pressure was maintained at 25–45 psi, by which time the rate of pressure drop was slow. Distillation gave a foreshot, 2.5 g, boiling below $30°$ C., followed by 16.7 g of crude product, bp $32°-77°$ C. The distillate was shown by GC and NMR analyses to be composed of 5% of unreacted perfluoropentene-2, 26% of the olefins perfluoro-2H-pentene-2/perfluoro-3H-pentene-2, 64% of perfluoro-2H,2H,3H-pentane and perfluoro-2H,3H,3H-pentane, and 13% of perfluoro-2H,3H-pentane. Thus the ratio of trihydro- to dihydropentanes was 83:17. It is expected that this ratio would be higher if the monohydroolefins were further reduced.

EXAMPLE 5

Reduction of Neat Liquid $CF_3CF=CFCF_2CF_3$

A mixture of 2.0 g of 5% Pd on carbon and 22.7 g (0.091 mol) of perfluoropentene-2 was agitated under 30–45 psi of hydrogen at $25°$ C. for two hours, after which hydrogen absorption slowed. The liquid product was shown by GC and NMR to contain an 83:17 ratio of dihydro- to trihydropentanes, with the perfluoro-2H,3H-dihydropentane present as two diastereomers in 90:10 ratio. Only 1% of the total product was unreacted perfluoropentene-2.

EXAMPLE 6

Reduction of neat Liquid F-Heptenes

Reduction of 44.2 g (0.126 mol) of perfluoroheptene-3/perfluoroheptene-2 mixture in a Parr hydrogenator with 2.8 g of 5% Pd on carbon at 25° C. proceeded readily at 20–50 psi of hydrogen. GC and MS indicated 3.5% of the crude product to be unreacted perfluoroheptenes, the rest being an 87:13 ratio of dihydro- to trihydropolyfluoroheptanes. Fractions of the product, bp 85°–94° C., were shown by NMR to contain perfluoro-3H,4H-heptane and perfluoro-2H,3H-heptane, in addition to the expected trihydro derivatives.

EXAMPLE 7

Reduction of $CF_3CF=CFCF_2CF_3$

A heavy-walled Parr bottle charged with 2.0 g of 5% Pd on carbon, 20.7 g (0.083 mol) of perfluoropentene-2, and 100 mL of dry DMF was kept under 20–50 psi of hydrogen while being shaken at 25° C. for 3 hours, after which time hydrogen absorption had nearly ceased. The mixture was treated with 4.2 g of NaF and distilled to give 17.6 g of crude product, bp 47°–48° C. After a wash with cold water and drying over $CaCl_2$, there was obtained 16.1 g (83%) of trihydrofluoropentanes as an 81:19 mixture of perfluoro-2H, 2H,3H-trihydropentane and perfluoro-2H,3H,3H-trihydropentane, identified by GC and NMR. NMR also indicated the presence of 4 mol-% of perfluoro-2H,3H-dihydropentane and 1 mol-% of perfluoro-2H,3H,3H-tetrahydropentane. This reaction provided a preferred polar solvent for very selectively reducing perfluorinated linear internal olefins to trihydro derivatives with hydrogen and metal catalyst under mild conditions.

EXAMPLE 8

Vapor Phase Reduction of $CF_3CF=CFCF_2CF_3$

A 6"×½" O.D. Hastelloy tube was charged with 10.0 g of 0.5% palladium on 5×8 mesh alumina spheres. This was a commercial sample from Calsicat which was reduced with hydrogen prior to use. Co-fed to the reactor were vaporized perfluoropentene-2 (2 mL/hr as liquid) and hydrogen (20 mL/min). Product stream leaving the reactor was analyzed by on-line GC and on-line MS, the product then being collected in a −80° C. trap during the run. At temperatures of 100°–200° C., conversions were 96–99% with yields of perfluoro-2H,3H-pentane consistently 95% or better over the temperature range. The level of trihydro by-product was ~1%. Product, bp 50°–55° C., easily obtained pure by a simple fractionation, was shown by GC and NMR analyses to have a ratio of diastereomers of about 90:10.

EXAMPLE 9

Reduction of $CF_3CF=CFCF_2CF_3$

Example 8 was substantially repeated except that the catalyst was 5.0 g of 1% ruthenium on carbon and the operating temperature was 200° C. Under these conditions perfluoropentene-2 conversion was 41.2% and the combined selectivity to the perfluoro-2H,3H-pentane isomers was 70.4%.

EXAMPLE 10

Reduction of $CF_3CF=CFCF_2CF_3$

A Parr bottle charged with 100 mL of methanol was blanketed with nitrogen while 2.0 g of 5% Pd on carbon was added, then cooled to 0° C. while 22.6 g (0.090 mol) of perfluoropentene-2 was added. The cold reactor was connected to the hydrogenation apparatus, purged three times with nitrogen, then pressured to 48 psi with hydrogen. The mixture was shaken at 25° C. for 4 hours while the hydrogen pressure was maintained at 12–48 psi; during this time the pressure dropped rapidly and then leveled. Calcium chloride (20 g) was added to the reaction mixture, and crude product was distilled, bp 45°–54° C. The distillate was washed with ice water and dried over anhydrous $CaCl_2$ to give 17.9 g (85%) of trihydropolyfluoropentanes, identified by GC and MS, and shown by NMR to be an 80:20 mixture of perfluoro-2H,2H,3H-trihydropentane and perfluoro-2H,3H,3H-trihydropentane. NMR also indicated the presence of about 3 mol-% perfluoro-2H,3H-dihydropentane and about 4 mol-% of perfluoro-2H,2H,3H,3H-tetrahydropentane.

This reaction demonstrated the high selectivity for formation of trihydro derivatives from linear, internal perfluoroolefins which can be achieved by carrying out a metal-catalyzed reduction in a polar liquid phase.

EXAMPLE 11

Reduction of Neat $CF_3CF=CFCF_2CF_3$

A chilled Parr bottle was charged with 2.05 g of 5% Rh on carbon, and 21.0 g (0.084 mol) of perfluoropentene-2, and was pressured to 50 psi using $H_2$. The mixture was shaken at 25° C. under 30–50 psi of $H_2$ until hydrogen uptake ceased (about 11 hours). The crude product was indicated by GC to contain 81% perfluoro-2H,3H-pentane (88:12 diastereomer ratio), and 19% trihydrononafluoropentanes, and was distilled from $CaCl_2$ to give 13.7 g of product, bp 46°–53° C. NMR showed the composition to be 77% dihydro/23% trihydropentanes.

EXAMPLE 12

Reduction of Neat $CF_3CF=CFCF_2CF_3$

Reduction of 20.9 g (0.08 mol) of perfluoropentene-2 and 10 g of 0.5% Pd on alumina was carried out at 25° C. under 30–50 psi of hydrogen over 13 hours. The resulting product was indicated by GC to contain a 72:28 ratio of dihydro- to trihydropolyfluoropentanes, with the perfluoro-2H,3H-pentane present as diastereomers in 94:6 ratio.

EXAMPLE 13

Reduction of $CF_3CF=CFCF_2CF_3$

A 500 mL Parr hydrogenator bottle was charged with 2.0 g of 5% Pd on carbon, 100 mL of nonane, and 20.9 g (0.084 mol) of perfluoropentene-2, pressured to 47 psi with hydrogen, and shaken at 25° C. for 6 hours while hydrogen pressure was maintained at 11–47 psi. Distillation afforded 16.5 g, bp 47°–53° C., indicated by NMR to contain dihydro- and trihydropentanes in 73:27 ratio, with perfluoro-2H,3H-pentane present as two diastereomers in 93:7 ratio.

EXAMPLE 14

Reduction of $CF_3CF=CFCF_2CF_3$

Reduction of 22.7 g (0.091 mol) of perfluoropentene-2 with 2.0 g of 5% Pd on carbon in 100 mL of toluene was carried out at 25° C. under ca. 20–50 psi of hydrogen until hydrogen absorption fell to 0.3 psi/hour. Distillation served to isolate volatiles, bp 25°–62° C., 18.3 g, which contained 65 wt-% of pentanes composed of 94:6 mol-ratio of dihydro- to trihydropentanes. The perfluoro-2H,3H-pentane consisted of diastereomers in a 97:3 ratio, an especially high selectivity.

This reaction demonstrated the unusually high selectivity for dihydrogenation of a perfluorinated linear internal olefin

EXAMPLE 15

Reduction of $CF_3CF=CFCF_2CF_3$

A reactor containing 20.0 g (0.080 mol) of perfluoropentene-2, 2.0 g of 5% Pd on carbon, and 100 mL of acetic acid was maintained under 30–50 psi of hydrogen while being shaken at 25° C. for 26 hours. Distillation afforded 10.1 g of liquid, bp 46°–55° C., which was little changed by a wash with ice-water. GC and NMR analyses indicated a 66:34 ratio of trihydropolyfluoropentanes to dihydropolyfluoropentanes.

Particular embodiments of the invention are included in the Examples. Other embodiments will become apparent to those skilled in the art from a consideration of the specification or practice of the invention disclosed herein. It is understood that modifications and variations may be practiced without departing from the spirit and scope of the novel concepts of this invention. It is further understood that the invention is not confined to the particular formulations and examples herein illustrated, but it embraces such modified forms thereof as come within the scope of the following claims.

What is claimed is:

1. A process for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, comprising the step of: hydrogenating an olefinic starting material in the liquid phase over a metal catalyst from the palladium group in the absence of a polar solvent; wherein said olefinic starting material has the same number of carbon atoms as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$; and wherein said olefinic starting material has its olefinic bond between the carbon atoms which correspond to the carbons which bear the hydrogen in said dihydropolyfluoroalkane.

2. A process in accordance with claim 1 wherein said olefinic starting material is hydrogenated over a palladium catalyst at a temperature in the range of from about 0° C. to about 200° C.; wherein the molar ratio of hydrogen to olefinic starting material is between 1:1 and 100:1; and wherein said linear dihydropolyfluoroalkane is the major product of said hydrogenation.

3. The process of claim 1 wherein the dihydropolyfluoroalkane is $CF_3CHFCHFCF_2CF_3$.

4. The process of claim 1 wherein the dihydropolyfluoroalkane is $CF_3CHFCHFCF_2CF_2CF_3$.

5. The process of claim 1 wherein the dihydropolyfluoroalkane is $CF_3CF_2CHFCHFCF_2CF_2CF_3$.

6. The process of claim 1 wherein the dihydropolyfluoroalkane is $CF_3CHFCHFCF_2CF_2CF_2CF_3$.

7. The process of claim 1 wherein the dihydropolyfluoroalkane is $CF_3CF_2CHFCHFCF_2CF_3$.

8. A process for preparing a linear dihydropolyfluoroalkane selected from the group consisting of $CF_3CHFCHFCF_2CF_3$, $CF_3CHFCHFCF_2CF_2CF_3$, $CF_3CF_2CHFCHFCF_2CF_2CF_3$, $CF_3CHFCHFCF_2CF_2CF_2CF_3$, and $CF_3CF_2CHFCHFCF_2CF_3$, comprising the step of: hydrogenating an olefinic starting material in the liquid phase over a metal catalyst from the palladium group in the absence of a polar solvent; wherein said olefinic starting material has the same number of carbon atoms as said dihydropolyfluoroalkane and is selected from the group consisting of $CF_3CF=CFCF_2CF_3$, $CF_3CF=CFCF_2CF_2CF_3$, $CF_3CF_2CF=CFCF_2CF_3$, $CF_3CF_2CF=CFCF_2CF_2CF_3$, and $CF_3CF=CFCF_2CF_2CF_2CF_3$; wherein said olefinic starting material has its olefinic bond between the carbon atoms which correspond to the carbons which bear the hydrogen in said dihydropolyfluoroalkane; and wherein said linear dihydropolyfluoroalkane is the major product of said hydrogenation.

9. The process of claim 8 wherein the dihydropolyfluoroalkane is $CF_3CHFCHFCF_2CF_3$.

10. A process in accordance with claim 9 wherein said olefinic starting material is hydrogenated over a palladium catalyst at a temperature in the range of from about 0° C. to about 200° C.; and wherein the molar ratio of hydrogen to olefinic starting material is between 1:1 and 100:1.

11. The process of claim 8 wherein the dihydropolyfluoroalkane is $CF_3CHFCHFCF_2CF_2CF_3$.

12. A process in accordance with claim 11 wherein said olefinic starting material is hydrogenated over a palladium catalyst at a temperature in the range of from about 0° C. to about 200° C.; and wherein the molar ratio of hydrogen to olefinic starting material is between 1:1 and 100:1.

13. The process of claim 8 wherein the dihydropolyfluoroalkane is $CF_3CF_2CHFCHFCF_2CF_2CF_3$.

14. A process in accordance with claim 13 wherein said olefinic starting material is hydrogenated over a palladium catalyst at a temperature in the range of from about 0° C. to about 200° C.; and wherein the molar ratio of hydrogen to olefinic starting material is between 1:1 and 100:1.

15. The process of claim 8 wherein the dihydropolyfluoroalkane is $CF_3CHFCHFCF_2CF_2CF_2CF_3$.

16. A process in accordance with claim 15 wherein said olefinic starting material is hydrogenated over a palladium catalyst at a temperature in the range of from about 0° C. to about 200° C.; and wherein the molar ratio of hydrogen to olefinic starting material is between 1:1 and 100:1.

17. The process of claim 8 wherein the dihydropolyfluoroalkane is $CF_3CF_2CHFCHFCF_2CF_3$.

18. A process in accordance with claim 17 wherein said olefinic starting material is hydrogenated over a palladium catalyst at a temperature in the range of from about 0° C. to about 200° C.; and wherein the molar ratio of hydrogen to olefinic starting material is between 1:1 and 100:1.

19. A process in accordance with claim 8 wherein said olefinic starting material is hydrogenated over a palladium catalyst at a temperature in the range of from about 0° C. to about 200° C.

20. A process in accordance with claim 8 wherein the molar ratio of hydrogen to olefinic starting material is between 1:1 and 100:1.

* * * * *